Jan. 3 , 1956 E. J. GARDNER Plant Pat. 1,445
MOCK ORANGE PLANT
Filed May 25, 1953
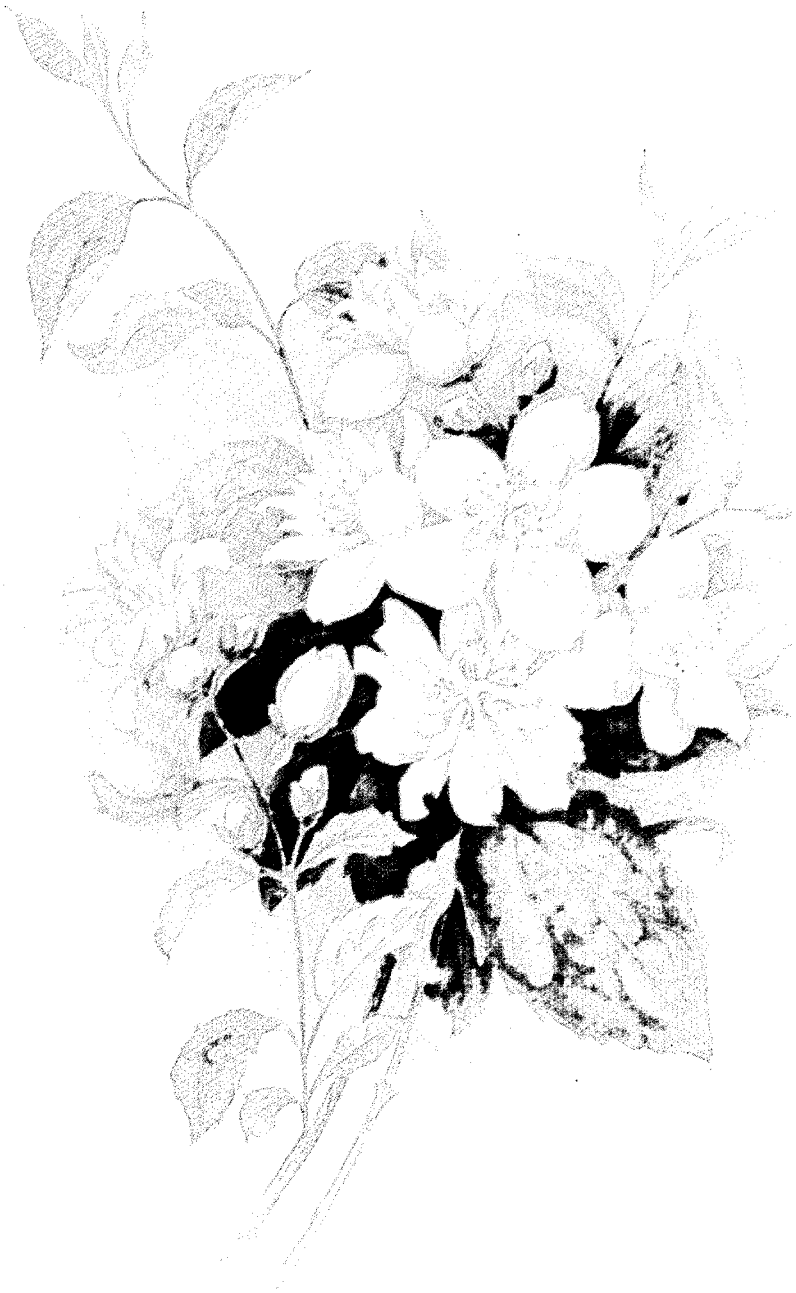
WITNESS
Addison J. Avery
INVENTOR
EDWARD J. GARDNER, DECEASED
BY ROBERT L. GARDNER, EXECUTOR
Wheeler, Wheeler & Wheeler
ATTYS.

United States Patent Office

Plant Pat. 1,445
Patented Jan. 3, 1956

1,445

MOCK ORANGE PLANT

Edward J. Gardner, deceased, late of Horicon, Wis., by Robert L. Gardner, executor, Horicon, Wis., assignor to Robert L. Gardner Application May 25, 1953, Serial No. 357,397

1 Claim. (Cl. 47—60)

This invention relates to a new variety of mock orange (Philadelphus) plant having unusually large and unusually double flowers particularly characterized by the multitude of small narrow petals within single or multiple rows of more conventional broad guard petals.

The drawing shows typical flowers, buds and leaves.

The original bush was a seedling of unknown ancestry raised from mixed seed of uncontrolled pollination collected from choice hybrid mock orange blooms. The original bush has been asexually reproduced by rooting cuttings therefrom at Horicon, Wisconsin.

The growth is vigorous. The young leaves are relatively lighter green than the fully developed leaves, the color being accurately reproduced in the drawing submitted.

The bloom occurs about the middle of June in the vicinity of Horicon, Wisconsin, or about the same time that Virginalis blooms. The blooms are in clusters of from two to eight. Each bloom is large or double having one or more rows of broad heavy petals. The outer petals are four in number in most cases, a few flowers with five petals being noted. When fully developed, the outer petals attain a broad elliptical form with full rounded margins and are relatively flat in extent.

Inner petals or petaloids are five to eight in number, frequently twisted. In addition, about half of the stamens develop into narrow curly petals which enhance the double appearance of the flower. All petals, including the outer petals, the inner petals or petaloids, and the specialized stamens are pure gleaming white in color. The pistils are nearly white with a greenish tinge and have a tip coloration identified in Maerz and Paul dictionary of color by plate 9–F–2 to 6. Stamens range in number from fourteen to twenty-three, averaging nineteen per bloom. The filaments are identified in Maerz and Paul by plate 9–B–1 and the anthers range in color between plate 9–K–3 and plate 9–I–4.

Sepals of the calyx are star-shaped, four in number, and pointed. The ovary is bulbous.

Having thus described some of the outstanding identifying characteristics of the mock orange bush of my invention, I claim:

A new and distinct variety of Philadelphus plant as described and illustrated and characterized by very double flowers including one or more rows of heavy broad outer petals surrounding a mass of narrow and generally twisted inner petals through which stamen project.

No references cited.